(12) United States Patent
Smith et al.

(10) Patent No.: US 12,198,799 B2
(45) Date of Patent: Jan. 14, 2025

(54) OPPORTUNISTIC DETECTION OF PATIENT CONDITIONS

(71) Applicants: Body Check, LLC, Hoover, AL (US); The UAB Research Foundation, Birmingham, AL (US)

(72) Inventors: Andrew Dennis Smith, Hoover, AL (US); Steven Adam Rothenberg, Vestavia Hills, AL (US); Yujan Shrestha, Castle Pines, CO (US)

(73) Assignees: Body Check, LLC, Hoover, AL (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 18/424,459

(22) Filed: Jan. 26, 2024

(65) Prior Publication Data
US 2024/0257947 A1    Aug. 1, 2024

Related U.S. Application Data

(60) Provisional application No. 63/482,524, filed on Jan. 31, 2023.

(51) Int. Cl.
*G16H 30/40* (2018.01)
*G06T 7/00* (2017.01)
(Continued)

(52) U.S. Cl.
CPC ........... *G16H 30/40* (2018.01); *G06T 7/0012* (2013.01); *G06T 7/11* (2017.01); *G16H 15/00* (2018.01);
(Continued)

(58) Field of Classification Search
CPC ........ G16H 15/00; G16H 50/20; G16H 30/40; G16H 10/60; G16H 20/00; G16H 30/00;
(Continued)

(56) References Cited

U.S. PATENT DOCUMENTS 9,792,681 B2 * 10/2017 Bryan ...................... G06N 7/01
2016/0361025 A1 * 12/2016 Reicher .................... G16Z 99/00
(Continued)

OTHER PUBLICATIONS

International Search Report and Written Opinion received for PCT Patent Application No. PCT/US24/13363, mailed on May 8, 2024, 14 pages.

*Primary Examiner* — Aaron W Carter
*Assistant Examiner* — Courtney Joan Nelson
(74) *Attorney, Agent, or Firm* — Workman Nydegger

(57) ABSTRACT

A system can be configured to: (i) obtain a set of input images depicting one or more bodily structures of a patient; (ii) determine whether one or more key structures are represented within the set of input images by utilizing a key structure detection module; (iii) determine one or more key images of the one or more images of the set of input images by utilizing a key image localization module; (iv) determine key structure segmentation by utilizing a key structure segmentation module; (v) determine one or more patient condition metrics using the key structure segmentation; and (vi) generate a report associated with the patient based upon the one or more patient condition metrics, or generate an entry at one or more practitioner worklists based upon the one or more patient condition metrics.

14 Claims, 11 Drawing Sheets

(51) Int. Cl.
  *G06T 7/11*    (2017.01)
  *G16H 15/00*   (2018.01)
  *G16H 30/20*   (2018.01)
(52) U.S. Cl.
  CPC .... *G06T 2207/30004* (2013.01); *G16H 30/20* (2018.01)
(58) Field of Classification Search
  CPC ...... G16H 10/00; G16H 30/20; G06T 7/0012; G06T 2207/30004; G06T 2210/41; G06T 7/70; G06T 7/00; G06T 7/11; A61B 8/5215; A61B 8/5292; A61B 8/5223; A61B 2018/00904; A61B 6/5217; A61B 5/0002; A61B 5/0013; G06V 2201/03; G06V 40/10; G06V 10/40; G06V 20/695; G06V 10/771; G06V 2201/07; G06V 30/19173; G06V 40/168
  See application file for complete search history.

(56) References Cited

U.S. PATENT DOCUMENTS

| | | | |
|---|---|---|---|
| 2018/0157799 A1* | 6/2018 | Ketterer | G16H 10/60 |
| 2018/0204327 A1  | 7/2018 | Matthews et al. | |
| 2019/0139218 A1* | 5/2019 | Song | G06N 3/044 |
| 2020/0321100 A1  | 10/2020 | Glottmann et al. | |
| 2020/0342990 A1* | 10/2020 | Ichinose | G16H 50/20 |
| 2021/0313049 A1  | 10/2021 | Khan et al. | |
| 2022/0160290 A1  | 5/2022 | Ejaz et al. | |
| 2023/0018833 A1  | 1/2023 | Das et al. | |

\* cited by examiner

400

402
Obtaining A Set Of Input Images, The Set Of Input Images Comprising One Or More Images, Each Of The One Or More Images Depicting One Or More Bodily Structures Of A Patient

404
Determining Whether One Or More Key Structures Are Represented Within The One Or More Images Of The Set Of Input Images By Utilizing The One Or More Images As Input To A Key Structure Detection Module, The Key Structure Detection Module Being Configured To Receive Image Input And Provide Key Structure Presence Indicator Output Based Upon The Image Input

406
Determining One Or More Key Images Of The One Or More Images Of The Set Of Input Images By Utilizing The One Or More Images As Input To A Key Image Localization Module, The Key Image Localization Module Being Configured To Receive Image Input And Provide Key Image Indicator Output Or Key Image Output

408
Determining Key Structure Segmentation By Utilizing The One Or More Key Images As Input To A Key Structure Segmentation Module, The Key Structure Segmentation Module Being Configured To Receive Image Input And Provide Region Of Interest Output

410
Determining One Or More Patient Condition Metrics Using The Key Structure Segmentation

412
(i) Generating A Report Associated With The Patient Based Upon The One Or More Patient Condition Metrics, Or (ii) Generating An Entry At One Or More Practitioner Worklists Based Upon The One Or More Patient Condition Metrics

414
Determining A Potential Patient Condition Based Upon Whether The One Or More Patient Condition Metrics Satisfy One Or More Thresholds Or Conditions

416
Determining Whether The Potential Patient Condition Comprises An Unmanaged Condition Based Upon (i) User Input Provided In Response To The Report Or The Entry At The One Or More Practitioner Worklists Or (ii) Output Of A Natural Language Processing Module Provided By Processing One Or More Electronic Medical Records Associated With The Patient

┌─ 502
Determining A First Potential Patient Condition Based Upon One Or More First Patient Condition Metrics, The One Or More First Patient Condition Metrics Being Determined Using (i) First Image Processing Output Of One Or More Image Processing Modules, The First Image Processing Output Being Generated Using A First Set Of Input Images Comprising One Or More First Images Depicting One Or More First Bodily Structures Of A First Patient And (ii) First Natural Language Processing Output Of One Or More Natural Language Processing Modules, The First Natural Language Processing Output Being Generated Using One Or More First Medical Imaging Reports Associated With The First Patient

↓ ┌─ 504
Generating A First Entry For The First Patient At A Practitioner Worklist Based Upon The First Potential Patient Condition

↓ ┌─ 506
Determining A Second Potential Patient Condition Based Upon One Or More Second Patient Condition Metrics, The One Or More Second Patient Condition Metrics Being Determined Using (i) Second Image Processing Output Of The One Or More Image Processing Modules, The Second Image Processing Output Being Generated Using A Second Set Of Input Images Comprising One Or More Second Images Depicting One Or More Second Bodily Structures Of A Second Patient And (ii) Second Natural Language Processing Output Of The One Or More Natural Language Processing Modules, The Second Natural Language Processing Output Being Generated Using One Or More Second Medical Imaging Reports Associated With The Second Patient

↓ ┌─ 508
Generating A Second Entry For The Second Patient At The Practitioner Worklist Based Upon The Second Potential Patient Condition

602 — Determining A Potential Patient Condition Based Upon One Or More Patient Condition Metrics, The One Or More Patient Condition Metrics Being Determined Using Image Processing Output Of One Or More Image Processing Modules, The Image Processing Output Being Generated Using A Set Of Input Images Comprising One Or More Images Depicting One Or More Bodily Structures Of A Patient

604 — Determining Or Configuring A Recommended Digital Therapeutic Based Upon The Potential Patient Condition For The Patient

606 — Adding The Recommended Digital Therapeutic To A Report Or An Entry Of A Practitioner Worklist In Association With The Patient

608 — Associating The Patient With A Patient Care Network Based Upon The Potential Patient Condition

*FIG. 6*

OPPORTUNISTIC DETECTION OF PATIENT CONDITIONS

CROSS-REFERENCE TO RELATED APPLICATIONS

This application claims priority to U.S. Provisional Patent Application No. 63/482,524, filed on Jan. 31, 2023, and entitled "OPPORTUNISTIC DETECTION OF PATIENT CONDITIONS", the entirety of which is incorporated herein by reference for all purposes.

BACKGROUND

Many individuals experience medical conditions that remain undetected until the individual undergoes medical screening and/or testing that is tailored to detecting such medical conditions. Such medical conditions can be asymptomatic (e.g., in early stages), which can cause a delay between the initial development of a medical condition in an individual and the performance of medical screening and/or testing to diagnose the medical condition. Such delay can allow medical conditions to advance, deepen, exacerbate, and/or aggravate before diagnosis and/or treatment can begin, which can cause undesirable outcomes for patients.

The subject matter claimed herein is not limited to embodiments that solve any disadvantages or that operate only in environments such as those described above. Rather, this background is only provided to illustrate one example problem space where some embodiments described herein may be practiced.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

The disclosure will be described and explained with additional specificity and detail through the use of the accompanying drawings in which:

FIGS. 4-6 illustrate example flow diagrams depicting acts associated with facilitating opportunistic detection of patient conditions.

DETAILED DESCRIPTION

Figure 1:
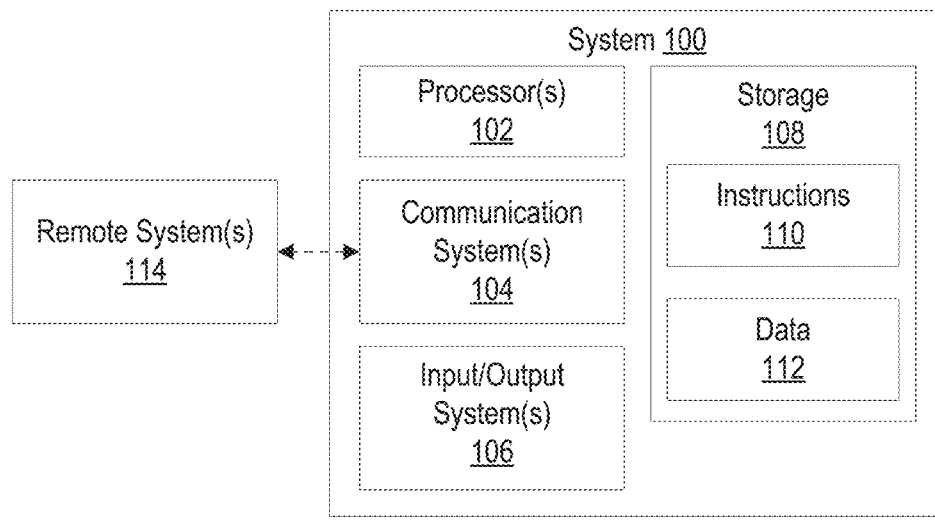
FIG. 1 illustrates an example system that may comprise or implement one or more embodiments of the present disclosure.

Before describing various embodiments of the present disclosure in detail, it is to be understood that this disclosure is not limited to the parameters of the particular example systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, any headings used herein are for organizational purposes only, and the terminology used herein is for the purpose of describing the embodiments. Neither are meant to be used to limit the scope of the description or the claims.

Embodiments of the present disclosure are directed to systems and methods for facilitating opportunistic detection of patient conditions.

As used herein, the term "physician" generally refers to a medical doctor, or a specialized medical doctor, such as a radiologist, primary care physician, cardiologist, or other medical doctor. This term may, when contextually appropriate, include any other medical professional or practitioner, including any licensed medical professional or other healthcare practitioners, such as a physician's assistant, a nurse, a veterinarian (such as, for example, when the patient is a non-human animal), etc.

The term "patient" generally refers to any entity under the care of a physician, with typical reference to humans who have undergone medical imaging. Such humans may include research participants, individuals under the care of a medical professional, and/or others. For the purpose of the present application, a "patient" may be interchangeable with an "individual" or "person." In some embodiments, the individual is a human patient.

Overview of Disclosed Embodiments

As used herein, opportunistic screening refers to passive screening for a particular medical condition using medical imagery and/or reports obtained for a purpose that is independent of screening for the particular medical condition. For instance, a physician may order routine cancer screening for a patient, and images of the patient acquired pursuant to the routine cancer screening may be analyzed/screened (e.g., in opportunistic fashion) to detect other medical conditions (e.g., cardiomegaly, coronary or aortic calcifications, aneurysms, and/or others).

At least some embodiments of the present disclosure are configured to utilize artificial intelligence (AI) and/or natural language processing (NLP) to opportunistically screen for multiple medical conditions within medical imagery and/or medical imaging reports. A few examples of medical conditions that are amenable to opportunistic screening as described herein include cardiovascular disease, endocrine conditions, chronic liver disease, low bone density or osteoporosis, kidney stones, chronic pulmonary disease, cancer, and/or others.

In some implementations, a system receives medical information such as medical images (e.g., DICOM-format medical images), text from medical image reports (e.g., radiograph, CT, MRI, echocardiogram, etc.), HL7 (Health Level 7) information, and/or text from electronic medical records (EMRs). The system may use the medical information to automatically detect one or more medical conditions and generate a summary report that includes key findings and data. In some instances, the summary report may include key images, segmentation maps, and/or statistical or measurement data.

The system may additionally or alternatively send the summary report to an RIS (research information system), PACS (picture archiving and communication system), EMR, and/or other database or data structure to enable the healthcare practitioner to review, accept, or reject the findings/results in the summary report. A healthcare practitioner may access the summary report to enable the healthcare practitioner to derive a medical management plan (which may include a referral to a digital therapeutic).

In some instances, the summary report (and/or findings represented in the summary report) are sent to a digital worklist or dashboard where a healthcare practitioner/provider can review and accept or reject the results/findings and optionally share aspects of the data with the patient. The healthcare provider may contact the patient and direct the patient to a clinical visit, direct the patient to a digital therapeutic (e.g., which may be recommended by the system based on the findings), etc. In some instances, systems may provide recommendations (based on the findings) for peer support or role model therapy (e.g., where users are responsible for coaching or supporting others with the same finding(s) and/or condition(s)).

The principles discussed herein may be implemented to facilitate opportunistic detection of various conditions and/or bodily structures or aspects that may be analyzed to detect disease states or other conditions, such as, by way of non-limiting example, cardiomegaly, coronary calcifications, aortic calcifications, aortic valve calcifications, pericardial effusion, aortic aneurysms, aortic dissection, intracranial aneurysms, other aneurysms (e.g., iliac, renal, splenic, etc.), pulmonary artery diameter (for pulmonary artery hypertension), specific cardiac chambers (RA, LA, RV, LV), chamber enlargement, moderate to severe valvular disease, systolic and diastolic dysfunction, body fat, liver fat, adrenal nodules, thyroid nodules, salivary gland nodules, pancreas volume, bone density, emphysema, interstitial lung disease/pulmonary fibrosis, bronchiectasis, small airways disease, lung nodules, pleural effusion, liver volume, liver fat, liver surface nodularity, cirrhosis, liver segmental volume ratio, splenomegaly, ascites, varices, liver mass, sarcopenia (muscle bulk/density), lung cancer, liver mass, pancreas mass or cyst, kidney mass, colon mass, lymphadenopathy, bone lesion, kidney stone, prostatomegaly, dental abnormalities, brain volume, brain anatomic compartment volumes, carotid calcifications, and/or others without limitation. As will be described in more detail hereinafter, any type of medical imagery may be utilized to facilitate opportunistic screening in accordance with the present disclosure.

Example Systems and Methods for Facilitating Opportunistic Detection of Patient Conditions Having described some of the various high-level features and benefits of the disclosed embodiments, attention will now be directed to FIGS. 1 through 6. These Figures illustrate various conceptual representations, architectures, methods, and/or supporting illustrations related to the disclosed embodiments.

FIG. 1 illustrates an example computer system 100 that may comprise or implement one or more embodiments of the present disclosure. As is illustrated in FIG. 1, the computer system 100 includes processor(s) 102, communication system(s) 104, I/O system(s) 106, and storage 108. Although FIG. 1 illustrates the computer system 100 as including particular components, it will be appreciated, in view of the present disclosure, that a computer system 100 may comprise any number of additional or alternative components.

The processor(s) 102 may comprise one or more sets of electronic circuitries that include any number of logic units, registers, and/or control units to facilitate the execution of computer-readable instructions (e.g., instructions that form a computer program). Such computer-readable instructions may be stored within storage 108. The storage 108 may comprise physical system memory and may be volatile, non-volatile, or some combination thereof. Furthermore, storage 108 may comprise local storage, remote storage, or some combination thereof. Additional details related to processors (e.g., processor(s) 102) and computer storage media (e.g., storage 108) will be provided hereinafter.

As used herein, processor(s) 102 may comprise or be configurable to execute any combination of software and/or hardware components that are operable to facilitate processing using machine learning models or other artificial intelligence-based structures/architectures. For example, processor(s) 102 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 may be configured to execute instructions 110 stored within storage 108 to perform certain actions. The actions may rely at least in part on data 112 stored on storage 108 in a volatile or non-volatile manner. In some instances, the actions may rely at least in part on communication system(s) 104 for receiving data from remote system(s) 114, which may include, for example, other computer systems or computing devices, medical imaging devices/systems, and/or others.

The communications system(s) 104 may comprise any combination of software or hardware components that are operable to facilitate communication between on-system components/devices and/or with off-system components/devices. For example, the communications system(s) 104 may comprise ports, buses, or other physical connection apparatuses for communicating with other devices/components (e.g., USB port, SD card reader, and/or other apparatus). Additionally, or alternatively, the communications system(s) 104 may comprise systems/components operable to communicate wirelessly with external systems and/or devices through any suitable communication channel(s), such as, by way of non-limiting example, Bluetooth, ultra-wideband, WLAN, infrared communication, and/or others.

Furthermore, in some instances, the actions that are executable by the processor(s) 102 may rely at least in part on I/O system(s) 106 for receiving user input from one or more users. I/O system(s) 106 may include any type of input or output device such as, by way of non-limiting example, a touch screen, a display, a mouse, a keyboard, a controller, and/or others, without limitation.

Some embodiments of the present disclosure can also be described in terms of acts (e.g., acts of a method) for accomplishing particular results. Although acts shown and/or described herein may be illustrated and/or discussed in a certain order, no particular ordering is required unless specifically stated or required because an act is dependent on another act being completed prior to the act being performed. Furthermore, it should be noted that not all acts represented in the drawings and/or description are essential for facilitating opportunistic detection of patient conditions in accordance with the present disclosure.

In some instances, the various acts disclosed herein are performed using a computer system 100. For instance, code/instructions for configuring the computer system 100 to perform the various acts disclosed herein may be stored as instructions 110 on storage 108, and such instructions 110 may be executable by the processor(s) 102 (and/or other components) to facilitate carrying out of the various acts.

FIGS. 2A-2F illustrate various components and functionalities of an example system 200 for facilitating opportunistic detection of patient conditions (e.g., which may include components of system 100). As depicted in FIG. 1, a system 200 may utilize a set of input image(s) 202 to facilitate opportunistic detection of patient conditions. The input image(s) 202 may include one or more images that depict one or more bodily structures of one or more patients. In this regard, the input image(s) 202 may comprise medical images acquired using medical imaging devices. For instance, the input image(s) 202 may include radiography images, computed tomography (CT) images, magnetic resonance imaging (MRI) images, positron emission tomography (PET) images, ultrasound images, variations thereof, and/or others. Although many examples discussed herein focus, in at least some respects, on utilizing 2D input images, the principles described herein may be applied to inputs comprising 3D representation of patient bodily structures (e.g., 3D objects/models depicting bodily structures of patients). Thus, the language "input image(s)" is not limited to 2D imagery, but may also include 3D or higher dimensional representations of patient bodily structures.

Figure 2A:
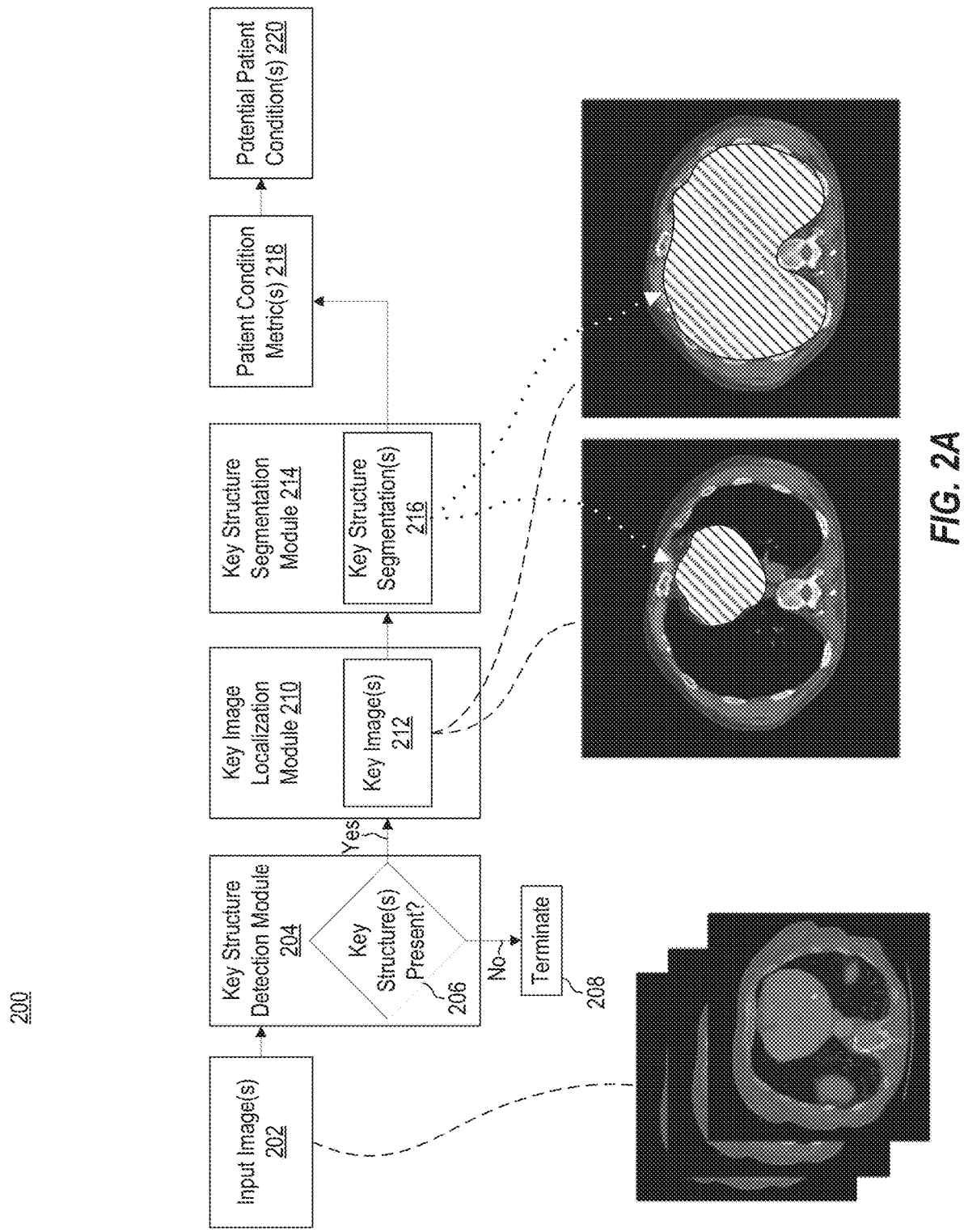
FIGS. 2A-2F illustrate various components and functionalities of an example system for facilitating opportunistic detection of patient conditions.

FIG. 2A conceptually depicts the input image(s) 202 as a series of cross-sectional images of a patient (e.g., CT images). The input image(s) 202 may include medical images acquired for any purpose, such as routine images captured to detect or evaluate cancer, tumors, emphysema, liver masses, internal bleeding and/or infections, bone and/or joint problems, causes of internal pain, and/or other purposes. Advantageously, as described herein, such images may be utilized to opportunistically screen for patient conditions that are not directly related to the purpose(s) for which the medical imaging was acquired.

The input image(s) 202 may capture the entire body of one or more patients or predefined portions of the body of one or more patients (e.g., the images may comprise a set of chest images, abdomen images, pelvis images, head images, etc.). The input image(s) 202 may include one or more sets of images that are associated with one or more respective patients. The input image(s) 202 may be stored in any suitable data repository (e.g., PACS, EMR, hospital/clinical database, etc.).

The system 200 may utilize the input image(s) 202 as input to a key structure detection module 204 to determine whether any key structures are present within the input image(s) 202 (as indicated in FIG. 2A by the decision block 206 associated with the key structure detection module 204). In some implementations, the key structure detection module 204 comprises one or more AI modules that is/are trained to receive image input and output an indication of whether a key structure is present within the input imagery. The key structure detection module 204 may take on various forms, such as a neural network based object classifier (e.g., utilizing convolutional network, YOLO, and/or other techniques). The output of the key structure detection module 204 (e.g., the key structure presence indicator) may include a binary output that indicates whether one or more key structures are present within the input image(s) 202 (or any subset(s) thereof; e.g., the key structure detection module 204 may output a separate key structure presence indicator for each subset of images included in the input image(s) 202). The binary nature of the output of the key structure detection module 204 is conceptually represented in FIG. 2A by the "Yes" and the "No" arrows extending from decision block 206 of the key structure detection module 204.

In some implementations, the key structure detection module 204 utilizes additional or alternative inputs, such as image metadata, image headers (e.g., DICOM headers), and/or other information to determine a key structure presence indicator. The key structure detection module 204 may be configured to detect the presence of various types of key structures within the input image(s) 202, such as, by way of non-limiting example, an organ, a body compartment, a cranial structure, a neck structure, a thoracic structure, an abdominal structure, a pelvic structure, an extremity structure, an intracranial structure, a cerebrospinal fluid space, a brain structure, a dental structure, a nervous structure, a spinal structure, a cardiovascular structure, a heart structure, a heart valve, a heart chamber, a pericardial structure, a vascular structure, a calcified vascular structure, a lung structure, an emphysematous structure, a pleural structure, a mediastinal structure, an esophageal structure, a thoracic muscle structure, a thoracic wall structure, a thoracic fat structure, a mammary or breast structure, an endocrine structure, a liver structure, a gallbladder structure, a biliary structure, a pancreas structure, a spleen structure, an adrenal structure, a kidney structure, a stomach or bowel structure, a body wall structure, an abdominal muscle structure, an abdominal fat structure, a subcutaneous fat structure, a visceral fat structure, a retroperitoneal structure, a peritoneal structure, a musculoskeletal or bone structure, a reproductive structure, a prostate structure, a uterine structure, an ovarian structure, a lymph node structure, a mass structure, a nodule structure, a cystic structure, a soft tissue structure, a fluid structure, a fat structure, a calcified structure, an aerated structure, a metallic structure, a medical device, a foreign body, a surgical structure, an artificial structure (e.g., a pacemaker), and/or others.

In some implementations, the key structure detection module 204 is configured to detect the presence of multiple different key structures (e.g., by implementing different sub-modules or module components trained to recognize different key structures). Each different sub-module or module component may output a respective key structure presence indicator for the input image(s) 202 (and/or image subsets thereof), indicating whether different key structures are present in the input image(s) 202 (and/or image subsets thereof).

If no key structure(s) is/are present in the input image(s) 202, processing of the input image(s) 202 may terminate (as indicated by decision block 208). As noted above, the determination of whether a key structure is present in the input image(s) may be made separately for different subsets of the input image(s) 202 and/or separately for different key structures for each subset. When one or more key structures are determined to be present in the input image(s) 202 (or a subset thereof), the input image(s) 202 may be utilized as input to a key image localization module 210 (as indicated in FIG. 2A by the "Yes" arrow extending from decision block 206).

As conceptually depicted in FIG. 2A, the key image localization module 210 is configured to receive image input and provide key image output (or key image indicator output, such as a slice position or other index indicating locations/positions of key images). In particular, the key image localization module 210 can be configured to identify key image(s) 212 from the input image(s) 202 that provide representation(s) of key structure(s) that is/are usable for further processing. As suggested above, separate key image(s) 212 may be identified for separate image subsets of the input image(s) 202 and/or different key structures present in the (subsets) of input image(s) 202. FIG. 2A conceptually depicts example key image(s) 212 that depict a cross-sectional representation of a chest cavity and heart of a patient. As suggested above, "key image(s)" is/are not limited to 2D images, but may additionally or alternatively include 3D representations of patient bodily structures.

The key image localization module 210 may comprise one or more AI modules and may take on various forms, such as a deep neural network (e.g., a regression deep neural network, which may be based on a VGG (visual geometry group) or other CNN architecture) or other forms. The key image localization module 210 may be configured to select key image(s) 212 from the input image(s) 202 based on one or more criteria, such as size, label/detection confidence, and/or other characteristics of the key structure(s) determined to be present in the input image(s) 202 (e.g., other visual characteristics). For instance, the key image(s) 212 depicted in FIG. 2A may be selected as images that provide the largest representation of the heart and/or chest cavity of a patient (e.g., relative to other images in the input image(s) 202 or a subset thereof associated with the particular patient).

FIG. 2A conceptually depicts that the key image(s) 212, as identified via the key image localization module 210, may be provided as input to a key structure segmentation module 214 (e.g., indicated by the arrow extending from the key image(s) 212 to the key structure segmentation module 214). The key structure segmentation module 214 of FIG. 2A is configured to determine key structure segmentation(s) 216 within the key image(s) 212 identified by the key image localization module 210. The key structure segmentation(s) 216 may take on various forms, such as region of interest output for the key structure(s) determined to be present by the key structure detection module 204. For example, the region of interest output may comprise a binary mask in the same coordinate system as the key image(s) 212 that indicates, for each pixel, whether the pixel belongs to the region of interest representing the key structure being segmented. As suggested above, "key structure segmentation(s)" is/are not limited to 2D segmentation (e.g., via a 2D pixel mask), but may additionally or alternatively include 3D segmentations of patient bodily structures (e.g., via a 3D voxel mask).

As indicated above, the key structure segmentation module 214 may output different key structure segmentation(s) 216 for different key image(s) 212 and/or for different key structures within the key image(s) 212 (e.g., multiple key structure segmentations may be determined within a single key image). For example, FIG. 2A provides a conceptual representation of different key structure segmentation(s) 216 depicted as regions of interest within the key image(s) 212, with one region of interest (left) representing a heart segmentation and the other region of interest (right) representing an inner chest segmentation. Such functionality may be useful, for instance, to determine a ratio between different structures within the same key image(s) 212, such as a ratio between the heart and inner chest cavity, a cardiothoracic index, and/or other metrics.

The key structure segmentation module 214 may comprise one or more AI modules (e.g., a deep neural network, such as a fully convolutional network, which may comprise a U-Net or other architecture) and/or may employ various segmentation techniques such as thresholding, clustering or dual clustering, compression or histogram based methods, edge detection, region growing, partial differential equation based methods, and/or others.

As indicated in FIG. 2A, the key structure segmentation(s) 216 may be utilized as input to determine patient condition metric(s) 218 (e.g., as indicated in FIG. 2A by the arrow extending from the key structure segmentation(s) 216 to the patient condition metric(s) 218). In some instances, the system 200 may utilize conventional measurement techniques to obtain the patient condition metric(s) 218 based upon the region of interest output of the key structure segmentation module 214 (e.g., area calculation, volume calculation, major axis length, minor axis length, structure height, structure width, Hounsfield unit (HU) values (e.g., mean, maximum, minimum), shape features, and/or others). In some instances, one or more AI modules may be employed to determine the patient condition metric(s) 218 (e.g., to predict key structure volume based on one or more key structure area inputs).

One will appreciate, in view of the present disclosure, that multiple patient condition metric(s) 218 and/or sets of patient condition metric(s) 218 may be determined for each key structure represented and segmented within the key image(s) 212. By way of example, each key structure in each key image associated with each patient (e.g., each patient associated with input image(s) 202) may have a respective set of patient condition metric(s) 218 determined therefor.

The patient condition metric(s) 218 (e.g., area, volume, length, height, major/minor axis length, HU values, etc.) determined based upon the key structure segmentation(s) 216 may be utilized to determine potential patient condition(s) 220 (as indicated in FIG. 2A by the arrow extending from the patient condition metric(s) 218 to the potential patient condition(s) 220). Different potential patient condition(s) 220 may be associated with different key structures for which key structure segmentation(s) 216 was/were obtained and for which patient condition metric(s) 218 were calculated. Various potential patient condition(s) 220 are within the scope of the present disclosure, such as, by way of non-limiting example, neurologic condition, dental conditions, cardiovascular conditions, endocrine conditions, pulmonary conditions, mammary conditions, musculoskeletal conditions, bone density conditions, gastrointestinal conditions, genitourinary conditions, liver conditions, biliary conditions, gallbladder conditions, pancreatic conditions, spleen conditions, adrenal conditions, kidney conditions, lymph node conditions, metabolic conditions, cancer conditions, reproductive conditions, and/or others.

In some implementations, the potential patient condition(s) 220 are determined based on the patient condition metric(s) 218 satisfying one or more thresholds or conditions. By way of non-limiting example, a potential patient condition 220 of cardiomegaly may be selected/determined in response to the patient condition metric(s) 218 of cardiothoracic index, heart to inner chest ratio, wall thickness, ventricular area, and/or others satisfying various thresholds or conditions. In some instances, the thresholds or conditions vary for different patients based upon patient attributes (at least some of which may be measured as patient condition metric(s) 218 or obtained from other patient information repositories, such as EMRs, image header data, image metadata, imaging notes, etc.). Example patient attributes may include, at least in the case of cardiomegaly, body mass index (BMI), height, weight, girth, age, gender, race, inner chest size (e.g., a surrogate for lean body mass), outer chest size (e.g., a surrogate for fat body mass), and/or others.

The potential patient condition(s) 220 may take on various forms and/or may include various components. For example, in some implementations, the potential patient condition(s) 220 may comprise one or more binary classifications (e.g., with different classifications for different conditions) for indicating whether a patient is likely experiencing a patient condition (e.g., "1") or likely not experiencing the patient condition (e.g., "0"). In other implementations, the potential patient condition(s) 220 comprise a more granular indication of the likelihood that a patient is experiencing one or more particular conditions. For instance, the potential patient condition(s) 220 may be represented as a plurality of qualitative levels (e.g., unlikely, slight likelihood, moderate likelihood, high likelihood) and/or a range of potential numerical values or scores that may indicate likelihood of one or more patient conditions. In some implementations, the potential patient condition(s) 220 comprise a plurality of available percentile ranks for patient condition metric(s) 218 associated with one or more patients (e.g., in the case of cardiomegaly, a percentile ranking of heart measurements for a particular patient relative to heart measurements of other patients with a similar age, gender, inner chest size, outer chest size, etc.).

As noted above, the potential patient condition(s) 220 may comprise multiple components, such as component for likelihood of experiencing a condition, a component for estimated severity of the condition, a component for expected degree of degradation over a time period, and/or others.

In some instances, the determination of the potential patient condition(s) 220 based upon the patient condition metric(s) 218 utilizes one or more AI modules (e.g., to calculate risk scores for patients based upon one or more models generated using one or more patient databases).

As noted above, multiple potential patient condition(s) 220 may be determined utilizing different (potentially overlapping) sets of key structure segmentation(s) 216 represented within key image(s) 212 (and/or other patient data). In this regard, in some instances, a key structure detection module 204 may be configured to detect additional key structures (e.g., in parallel, via the key structure detection module 204 comprising multiple sub-modules or modules), the key image localization module 210 may be configured to determine additional key images (e.g., in parallel, via the key image localization module 210 comprising multiple sub-modules or modules), and/or the key structure segmentation module 214 may be configured to determine additional key structure segmentation (e.g., in parallel, via the key structure segmentation module 214 comprising multiple sub-modules or modules). Similarly, a system 200 may be configured to determine additional patient condition metrics and/or potential patient conditions based upon the additional key structure segmentation (e.g., in parallel).

Figure 2B:
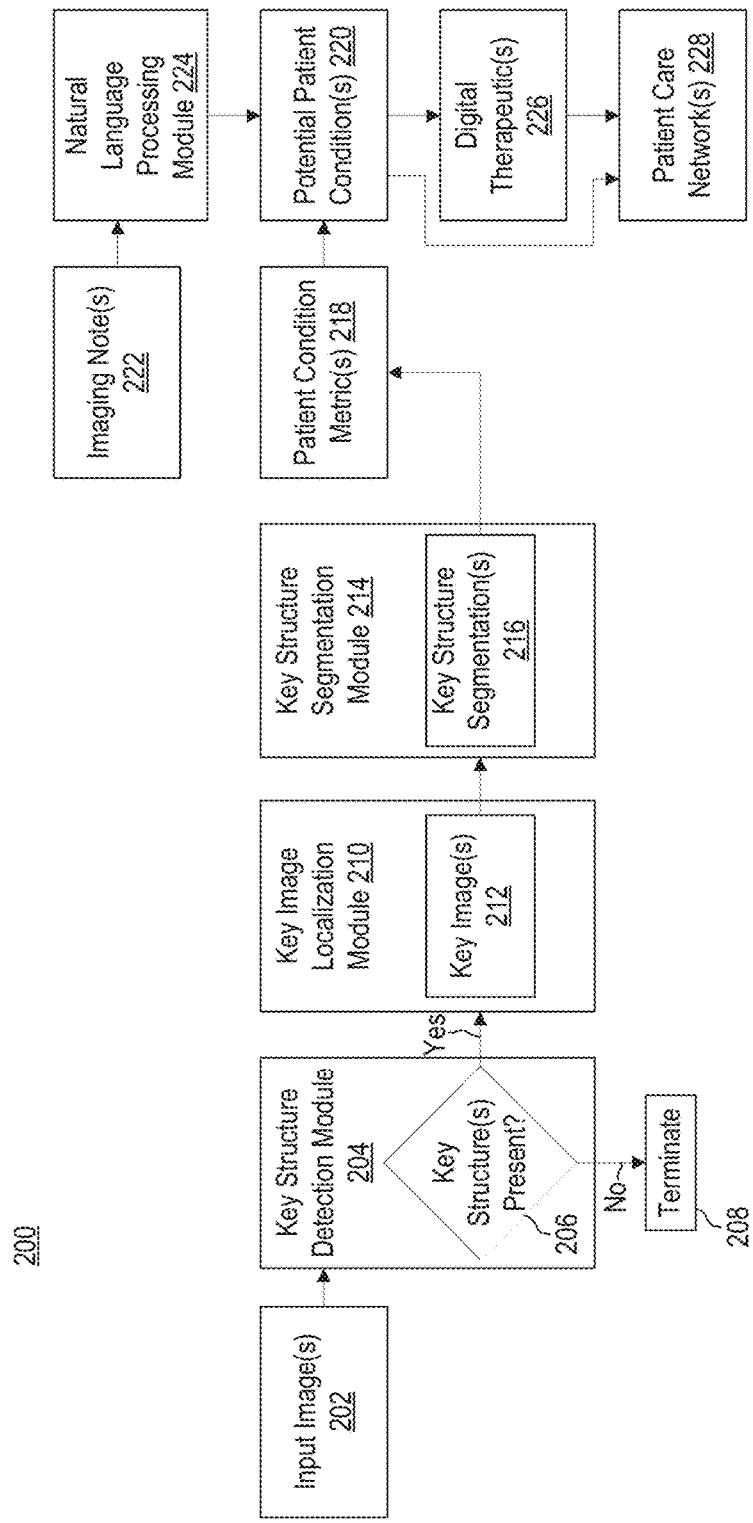

In some implementations, the system 200 is configured to utilize additional information to determine the potential patient condition(s) 220. For instance, FIG. 2B depicts imaging note(s) 222, which may be obtained based upon user input of practitioners acquiring or reviewing medical imagery (e.g., CT notes/reports, echocardiogram notes, and/or other notes associated with the input image(s) 202 and/or the patients represented in the input image(s) 202). As used herein, "imaging note(s)" refers broadly to any health record data and/or non-image data pertinent to one or more patients. As depicted in FIG. 2B, the imaging note(s) 222 may be utilized as input to a natural language processing module 224 trained to detect indications of potential patient conditions within the imaging note(s) 222. The potential patient condition(s) 220 may thus additionally or alternatively be based upon output of the natural language processing module 224 (e.g., generated by processing the imaging note(s) 222).

FIG. 2B also depicts that the system 200 may, in some instances, determine digital therapeutic(s) 226 and/or patient care network(s) 228 that may be recommended for patients based on the potential patient condition(s) 220 determined for the patients (e.g., based upon image processing of the input image(s) 202 by the various modules of the system 200). Digital therapeutic(s) 226 may comprise therapeutic interventions driven by software (e.g., computer-executable instructions) and configured to prevent, manage, and/or treat medical disorders, diseases, and/or conditions (e.g., by facilitating behavioral and/or lifestyle changes by digital prompts/impetuses). Digital therapeutic(s) 226 may be implemented on various types of computing devices/user interfaces, such as, by way of non-limiting example, desktop computers, tablets, laptops, smartphones (or other mobile electronic devices, such as watches, rings, etc.), head-mounted displays (e.g., virtual reality, augmented reality, or other extended reality displays/devices), and/or others. By way of example, digital therapeutic(s) 226 may include exercise programs that may be facilitated utilizing sensor technology (e.g., utilizing computer vision for pose estimation) to track patient performance, compliance, and/or progress. In some instances, digital therapeutic(s) 226 utilize gamification and/or rewards to facilitate compliance tracking. Data obtained indicative of usage and/or compliance may be made available to medical practitioners (e.g., the prescribing physician), health systems (e.g., to track population health), and/or payers (e.g., which may influence insurance premium adjustments).

The digital therapeutic(s) 226 may comprise prescription and/or non-prescription programs and may measure and/or provide insights on patient results, goals, engagement, and/or outcomes (in a secure manner). Digital therapeutic(s) 226 may include therapies for addressing comorbidities, side effects, and/or affiliated conditions. Digital therapeutic(s) 226 may provide treatments that produce direct neurologic changes, deliver cognitive behavioral therapy (and/or other evidence-based treatments), deliver responsive physical exercises and/or behavioral interventions, etc. The digital therapeutic(s) 226 may be utilized independently or in concert with medications, devices, and/or other therapies (e.g., in-person therapies). In some implementations, aspects of the digital therapeutic(s) 226 are personalized for specific patients (e.g., based upon the patient condition metric(s) 218, the potential patient condition(s) 220, other medical or personal information about the patient, such as age, weight, BMI, sex, other medical conditions, etc.).

By way of non-limiting example, in response to detecting a potential patient condition 220 of low bone mineral density for a patient, a digital therapeutic 226 that includes a dietary and/or exercise regimen tailored to increasing bone mineral density may be recommended for the patient (e.g., the digital therapeutic 226 may be provided to a user device of the patient, such as by downloading of a mobile device application). In some implementations, the dietary and/or exercise regimen for the patient are derived based upon risk factors and/or other information specific to the patient, such as age, gender, medications, etc. In some instances, a patient care network 228 may be recommended for the patient that includes other patients also experiencing low bone mineral density (or any other common medical condition(s)), enabling patients to provide one another with peer to peer support, mentorship, coaching. In some instances, peer to peer coaching and/or participation may be incentivized by payments to coaches and/or insurance premium reductions.

As another example, in response to detecting a potential patient condition 220 of cardiovascular disease for a patient, a digital therapeutic 226 that includes a dietary and/or exercise regimen tailored to improving cardiovascular health may be recommended for the patient. A patient care network 228 may be recommended for the patient that includes other patients also experiencing cardiovascular disease.

In some instances, patients may be automatically enrolled in the digital therapeutic(s) 226 and/or recommendations for the digital therapeutic(s) 226 may be pushed to patient and/or practitioner devices (e.g., for patients already subscribed to a digital therapeutic platform). In some instances, the recommended digital therapeutic(s) 226 are generated for potential patient condition(s) 220 that are determined to be unmanaged (e.g., based upon user input provided in response to a report or worklist entry, or based upon NLP output, as will be described in more detail hereinafter).

Figure 2C:
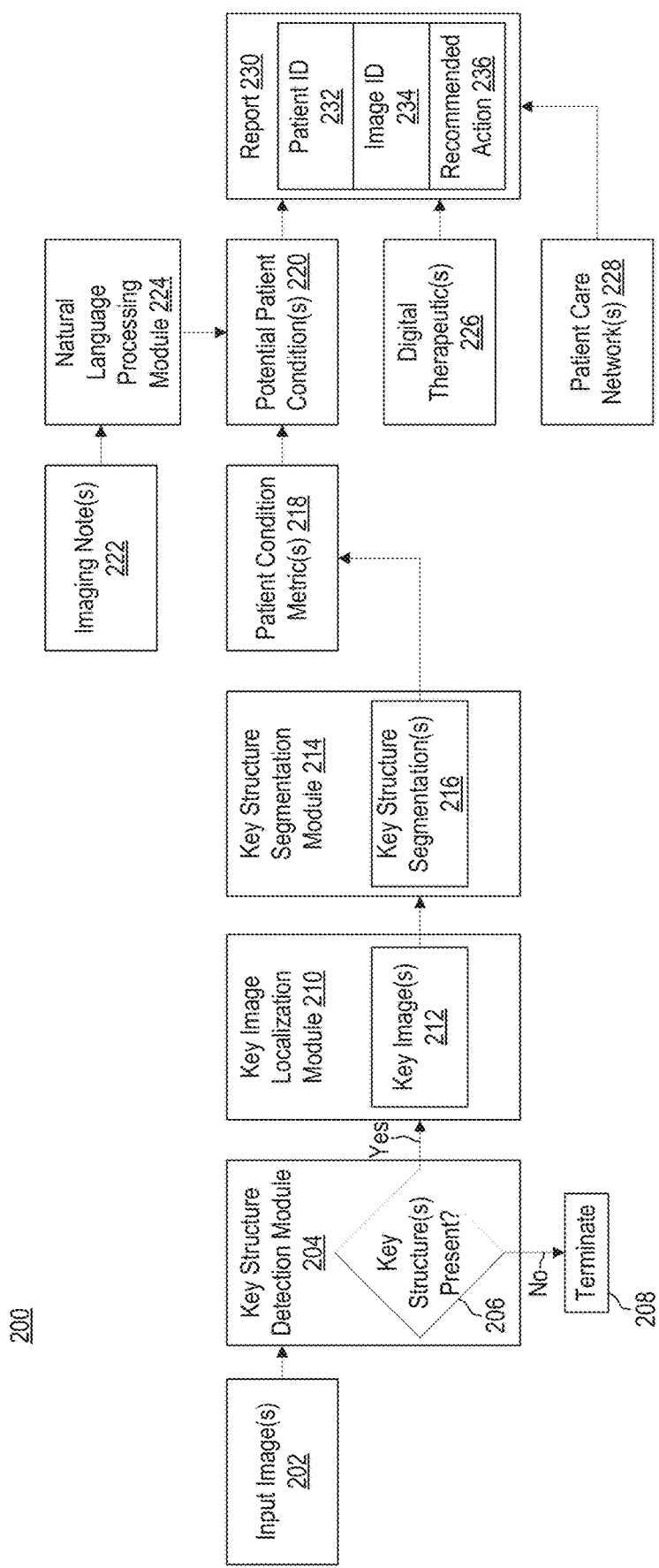

In some implementations, the system 200 is configured to generate a report 230 based upon the potential patient condition(s) 220 (and/or the patient condition metric(s) 218, the digital therapeutic(s) 226, and/or the patient care network(s) 228), as depicted in FIG. 2C. In some instances, the system 200 generates the report 230 (e.g., via a report generation module that performs data aggregation/gathering tasks) in response to determining that potential patient condition(s) 220 exist in one or more particular patients (e.g., in response to determining that the patient condition metric(s) 218 satisfy one or more thresholds or conditions).

The report 230 may comprise various information (which may come from various sources, such as imagery, image headers, imaging notes, EMRs, and/or others). In the example of FIG. 2C, the report 230 is conceptually depicted as including the potential patient condition(s) 220, the digital therapeutic(s) 226, the patient care network(s) 228, a patient ID 232 (e.g., identifying information for the patient to whom the report pertains), an image ID 234 (e.g., identifying information for key image(s) 212, or representations of the key image(s) 212 and/or the key structure segmentation(s) 216), and/or recommended action 236 (e.g., for practitioners and/or patients to take to accept, reject, or otherwise respond to or act upon the information in the report 230). A report 230 may include additional or alternative components not explicitly shown in FIG. 2C. In some instances, a report 230 may include information associated with multiple potential patient conditions for a single patient (e.g., based upon multiple key structures detected in one or more key images for a single patient).

In some instances, a report 230 may display information and/or outputs of the various modules of the system 200 (e.g., outputs utilized to determine the presence of the potential patient condition(s) 220, such as the key image(s) 212, the key structure segmentation(s) 216, sections of imaging note(s) 222, etc.). In some instances, the report 230 may be presented to practitioners with functionality enabling practitioners to accept or reject/modify the findings and/or outputs of the modules of the system 200. Such user modifications may be utilized to further train the various modules of the system (e.g., the key structure detection module 204, the key image localization module 210, the key structure segmentation module 214, recommendation modules, etc.).

Figure 3:
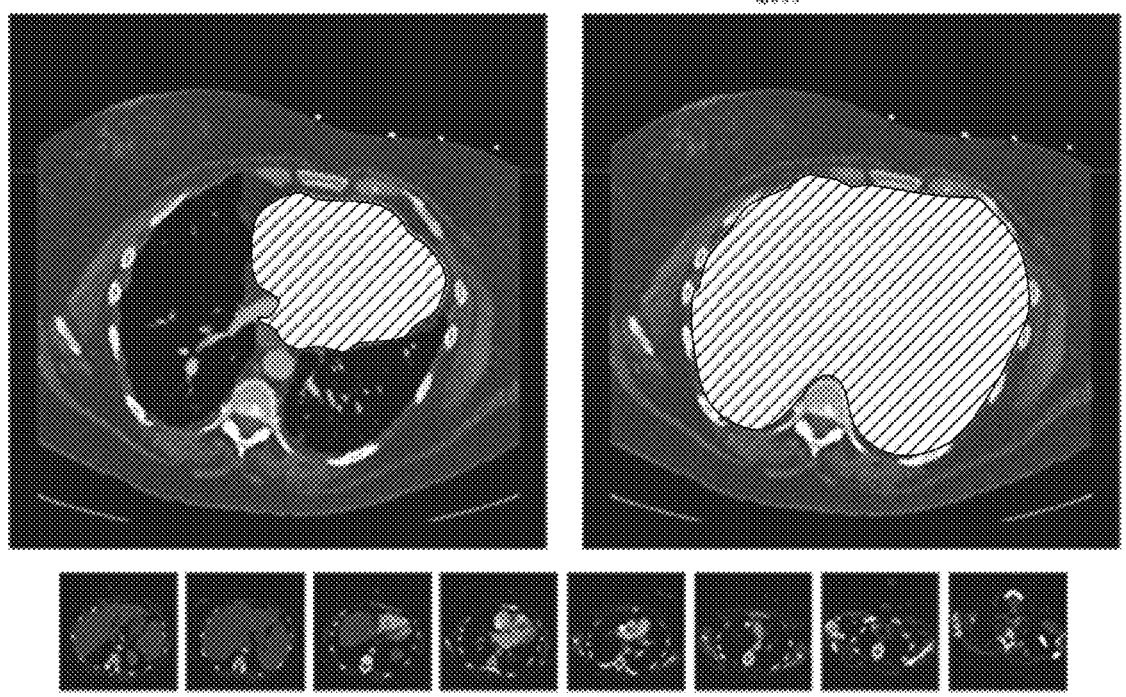
FIG. 3 illustrates example aspects of a report generated based on output of a system for facilitating opportunistic detection of patient conditions.

Attention is briefly directed to FIG. 3, which provides an example depiction of a report (e.g., report 230). In the example of FIG. 3, the report includes patient identifying information, image identifying information, various patient condition metrics (e.g., cardiothoracic index, heart to inner chest ratio, etc.), key images, and key structure segmentation (e.g., overlaid on the key images). The report also includes reference ranges for measurements (e.g., as applicable to the particular patient and/or a population of which the patient is a part). Practitioners may modify the reference ranges based upon their clinical judgment and/or standard of care. A report (e.g., report 230) may be sent to PACS or other interfaces/databases to enable display and distribution to medical practitioners.

Figure 2D:
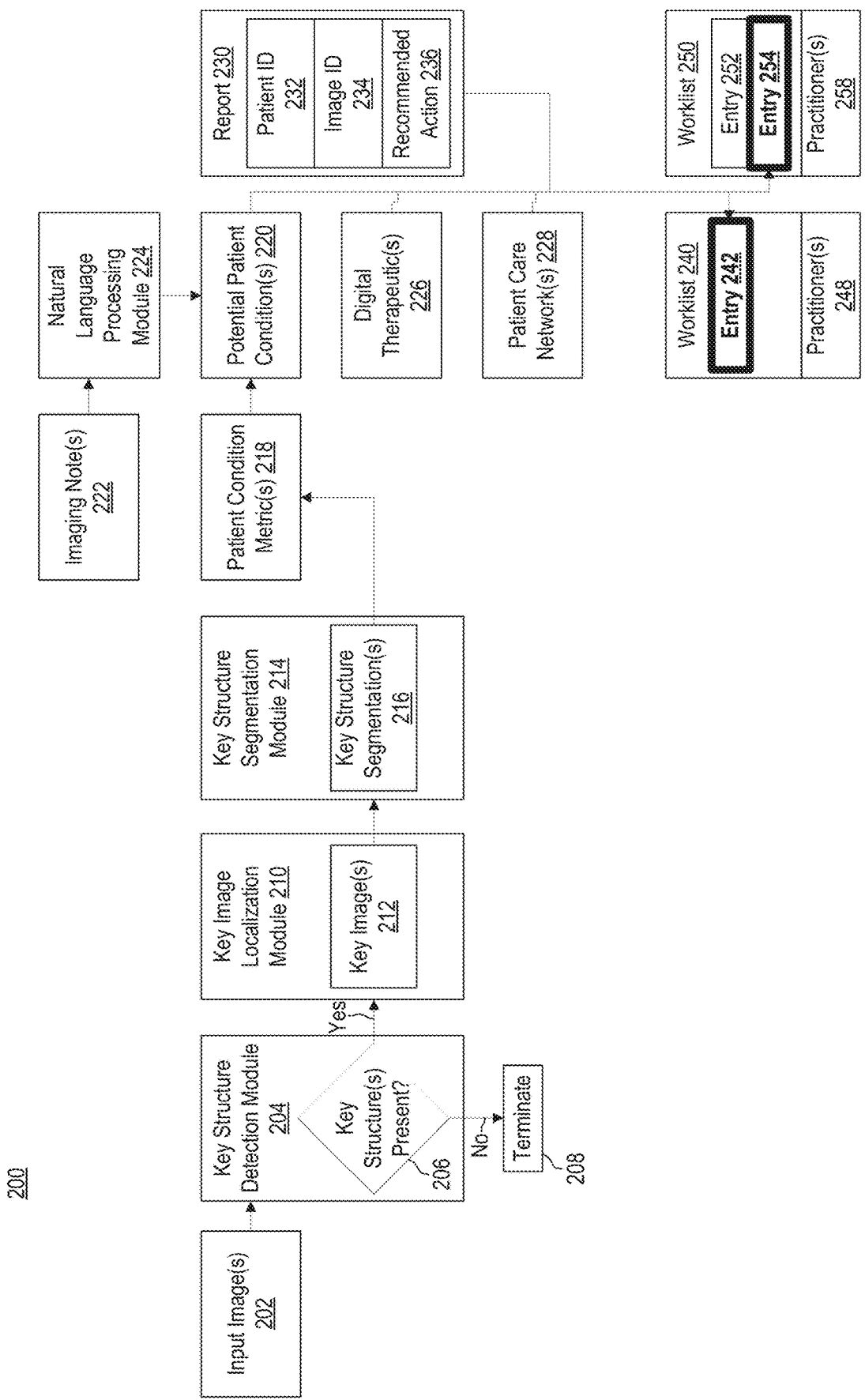

Attention is directed to FIG. 2D, which conceptually depicts that the system 200 may additionally or alternatively be configured to generate one or more entries at one or more practitioner worklists based upon the potential patient condition(s) 220 and/or other information. FIG. 2D illustrates that the potential patient condition(s) 220, the digital therapeutic(s) 226, the patient care network(s) 228, the report 230, and/or any information of the report 230 or upon which the report is based may be utilized to generate an entry 242 at a worklist 240 (e.g., a practitioner worklist). In some instances, the entry 242 may be regarded as the report 230 or a representation thereof or a link/portal thereto. The entry 242 may be associated with a particular patient for whom a potential patient condition was detected. In some instances, an entry at a worklist in association with a patient (or a report for a patient) is generated in response to determining that a potential patient condition exists for the patient (e.g., based on processing of the input image(s) 202 and/or imaging note(s) 222).

The worklist 240 (e.g., a practitioner worklist) may comprise a work queue associated with one or more medical practitioners 248 (e.g., practitioners of a particular subspecialty) that may include tasks for the practitioner(s) 248 to perform and/or items for the practitioner(s) 248 to review to facilitate patient care. In some instances, the worklist 240 and/or the practitioner(s) 248 are associated with a particular medical subspecialty and/or a particular set of medical conditions, such that entries (e.g., entry 242) that are generated at or added to the worklist 240 are also associated with the same medical subspecialty and/or particular subset of medical conditions.

For example, the practitioner(s) 248 may have training enabling them to diagnose cardiomegaly (or another condition) from medical imagery (e.g., CT images). The practitioner(s) 248 may have access to the worklist 240 (e.g., via a user profile system), and the worklist 240 may include entries associated with cardiomegaly (or another condition). For instance, in response to the system 200 determining that a potential patient condition 220 for a particular patient is cardiomegaly (or another condition) (e.g., based upon patient condition metrics 218 derived from key structure segmentation 216 on a key image 212 from input images 202 associated with the particular patient), the system 200 may add the entry 242 to the worklist 240 in association with the particular patient, which may prompt the practitioner(s) 248 to review the entry 242 (and/or report 230) to accept, reject, or modify the findings of the system 200 (e.g., to accept, reject, or modify the determination of whether a key structure is present as indicated by the key structure detection module 204, to accept, reject, or modify the selection of key image(s) 212 as identified by the key image localization module 210, to accept, reject, or modify the key structure segmentation 216 as provided by the key structure segmentation module 214, to accept, reject, or modify the potential patient condition(s) 220 or recommended digital therapeutic(s) 226 or recommended patient care network(s) 228 as output by the system, etc.). As noted above, such user input accepting, rejecting, or modifying the findings/output/ recommendations of the system 200 may be utilized to further train/refine the modules of the system.

FIG. 2D also depicts an additional worklist 250, which may be associated with a different (potentially overlapping) set of practitioner(s) 258, medical subspecialty, or subset of potential patient condition(s) 220 than the worklist 240. In this regard, when the system 200 detects a different or additional potential patient condition 220 for a patient (e.g., based upon different or additional patient condition metrics 218 derived from different or additional key structure segmentation 216 on a key image 212 from input images 202), the system may add the entry 254 to the worklist 250 in association with the patient, which may prompt the practitioner(s) 258 to review the entry 254 (and/or corresponding report) to accept, reject, or modify the findings of the system 200. Accordingly, a system 200 may process input image(s) 202 and/or imaging note(s) 222 to detect different potential patient condition(s) 220 (within the same or different patients) to cause generation of entries at worklists associated with different practitioners and/or different medical subspecialties.

In view of the foregoing, a practitioner worklist may include entries associated with multiple different patients. For instance, a system 200 may determine a first potential patient condition 220 for a first patient (e.g., based upon image processing and/or NLP output) and may generate a first entry 252 based upon the first potential patient condition 220 at worklist 250. The system 200 may similarly determine a second potential patient condition 220 (which may be the same type of condition as the first potential patient condition) for a second patient (e.g., based upon image processing and/or NLP output) and may generate a second entry 254 based upon the second potential patient condition 220 at worklist 250. The practitioner(s) 258 may thus be prompted to review both entries 252 and 254 for the different patients using the same worklist 250.

Figure 2E:
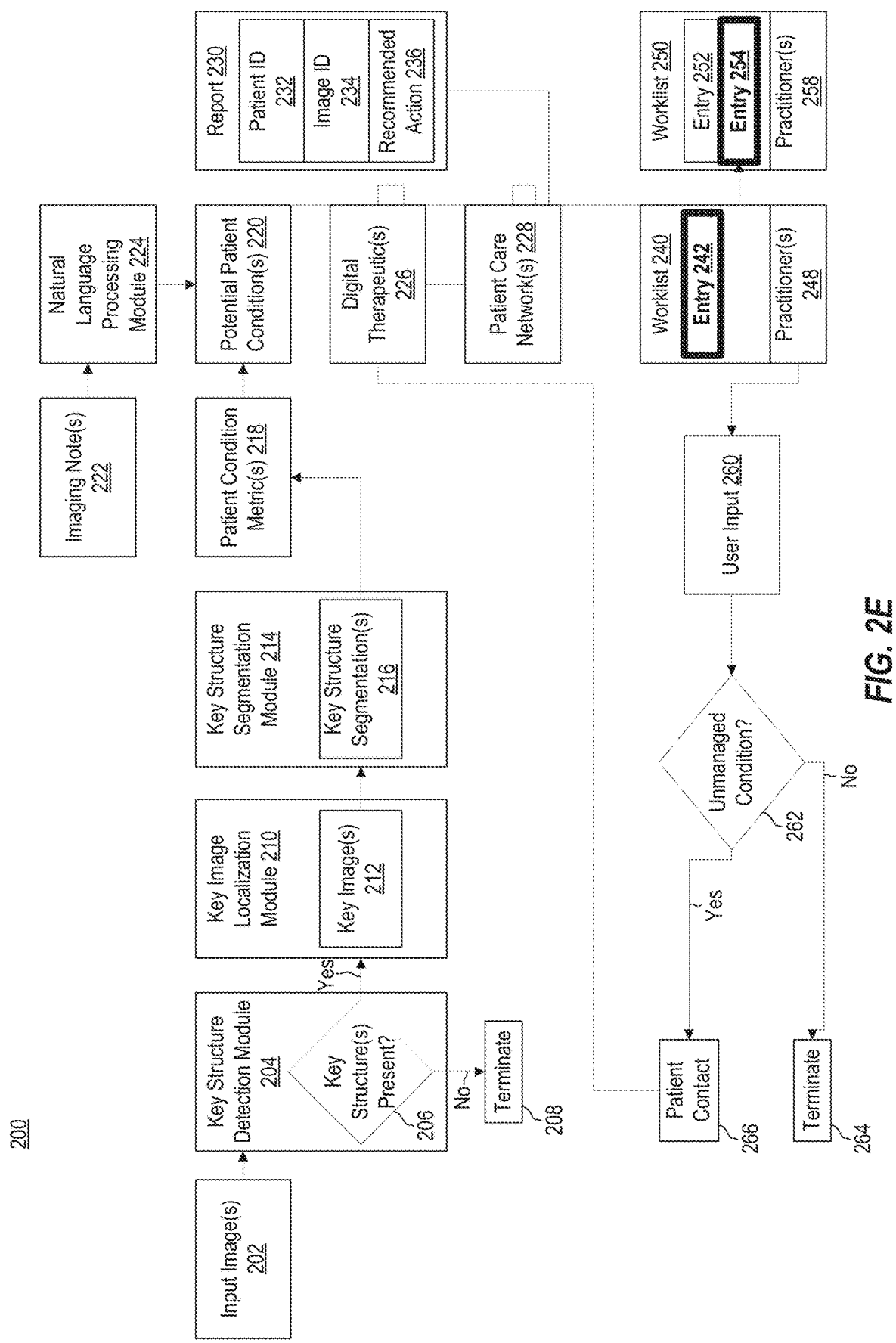

As indicated above, access to the worklists and/or reports generated and/or updated by the system 200 may be sent to one or more devices associated with healthcare practitioners to enable the practitioners to perform certain actions in response to the worklist entries and/or reports. FIG. 2E illustrates an example in which the practitioner(s) 248 provide user input 260 in response to the entry 242 or a corresponding report 230 (e.g., after verifying the accuracy of a potential patient condition 220 associated with the entry 242 and/or report 230) indicating whether the potential patient condition 220 associated with the entry 242 is an unmanaged condition (as indicated in FIG. 2E by decision block 262).

For instance, in an illustrative example where the entry 242 and/or corresponding report 230 are associated with a potential patient condition 220 of cardiomegaly for a particular patient (or another condition), the practitioner(s) 248 may access medical records (e.g., EMRs) and/or other data associated with the particular patient to determine whether cardiomegaly (or another condition) is already being managed for the particular patient. In the example of FIG. 2E, in response to determining that cardiomegaly (or another condition) is already being managed for the particular patient, the practitioner(s) 248 (or other users) may provide further input terminating further processing of the entry 242 (e.g., as indicated by action block 264 in FIG. 2E). In contrast, in response to determining that cardiomegaly (or another condition) is not being managed for the particular patient, the practitioner(s) 248 (or other users) may initiate patient contact and/or other care actions to facilitate management of cardiomegaly (or another condition) for the particular patient (e.g., as indicated by action block 266 in FIG. 2E). For instance, initiating patient contact may include inviting the particular patient to a clinical visit, providing information/findings to the patient, etc. In some instances, initiating patient contact (e.g., in accordance with action block 266) may comprise generating, modifying/personalizing/configuring, prescribing, recommending, and/or enrolling the digital therapeutic(s) 226 to the patient (as indicated in FIG. 2E by the dashed line extending from action block 266 to the digital therapeutic(s) 226).

In some instances, upon determining that a potential patient condition 220 is already being managed, a system may add an entry, in association with the particular patient, to a database to prevent future duplicative opportunistic screening efforts for the particular patient. For instance, in response to determining that cardiomegaly (or another condition) is already being managed for the particular patient, an entry may be added to the database explicitly indicating that cardiomegaly (or another condition) is already being managed for the particular patient. When the system processes future input image(s) 202 of the particular patient, the system 200 may access the database and determine that cardiomegaly (or another condition) are already being managed for the patient, which may cause the system to selectively refrain from performing key structure detection, key image selection, and/or key structure segmentation for structures used to assess the presence of cardiomegaly (or another condition). The system may also selectively refrain from generating additional reports, worklist entries, recommended digital therapeutics, recommended patient care networks, etc.

Figure 2F:
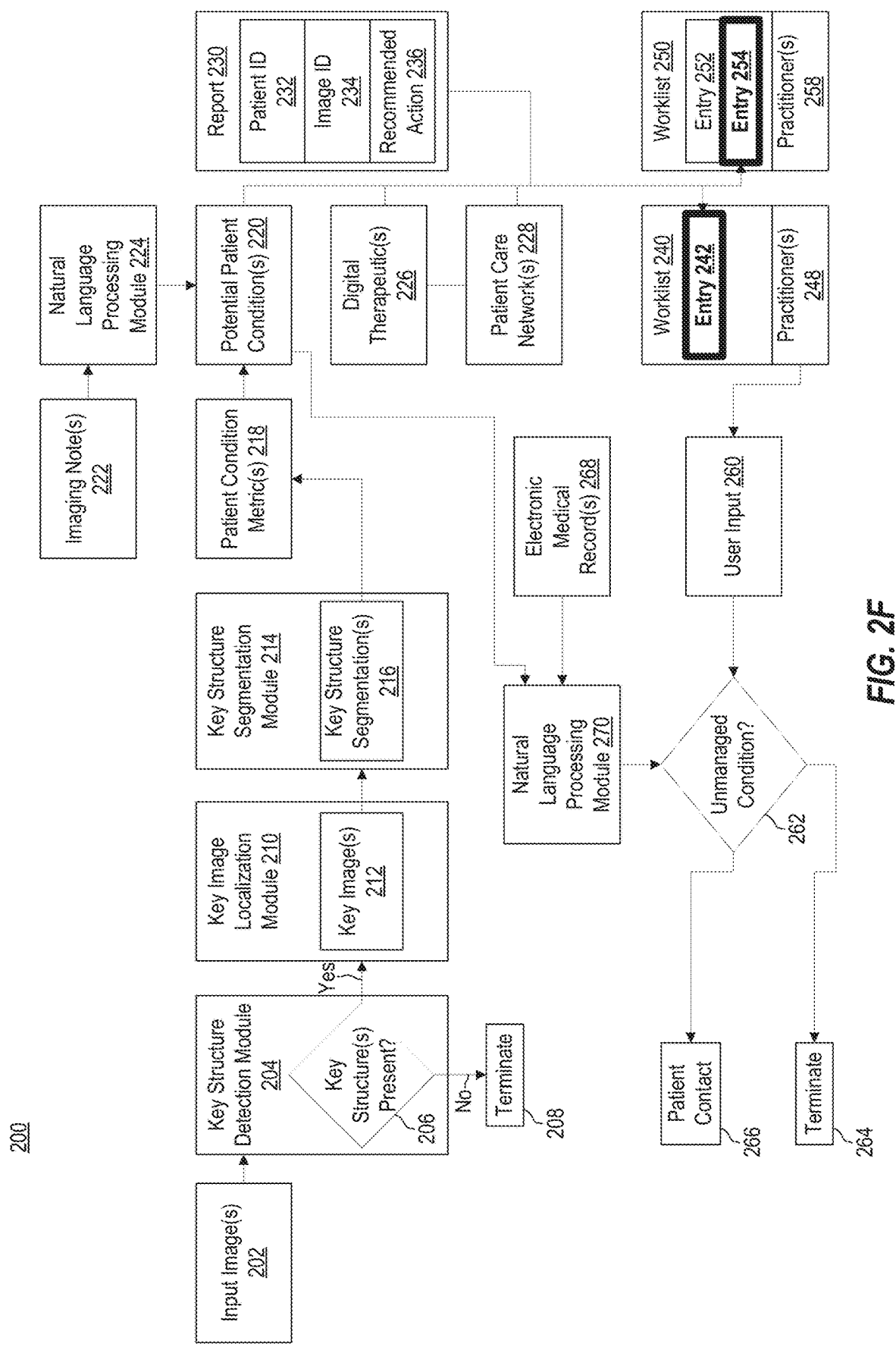

In some implementations, a system 200 utilizes additional or alternative techniques to determine whether a potential patient condition is unmanaged. FIG. 2F illustrates an example in which the system 200 utilizes the potential patient condition(s) 220 for a patient and electronic medical record(s) 268 for the patient as input to a natural language processing module 270 to determine whether the potential patient condition(s) 220 is/are unmanaged for the patient (decision block 262 in FIG. 2F). For example, the natural language processing module 270 may search through the electronic medical record(s) 268 and/or other data for the patient for terms, ICD, and/or CPT codes that would indicate that the patient has been diagnosed or is being treated for the potential patient condition(s) 220.

FIGS. 4-6 illustrate example flow diagrams 400, 500, and 600, respectively, depicting acts associated with facilitating opportunistic detection of patient conditions.

Act 402 of flow diagram 400 of FIG. 4 includes obtaining a set of input images, the set of input images comprising one or more images, each of the one or more images depicting one or more bodily structures of a patient. In some instances, the set of input images comprises one or more radiography images, computed tomography images, magnetic resonance imaging images, positron emission tomography images, or ultrasound images.

Act 404 of flow diagram 400 includes determining whether one or more key structures are represented within the one or more images of the set of input images by utilizing the one or more images as input to a key structure detection module, the key structure detection module being configured to receive image input and provide key structure presence indicator output based upon the image input. The key structure detection module may comprise one or more AI modules.

In some implementations, the key structure presence indicator output comprises binary output indicating whether the one or more key structures are present in any of the one or more images of the set of input images. In some instances, the one or more key structures comprise one or more of: an organ, a body compartment, a cranial structure, a neck structure, a thoracic structure, an abdominal structure, a pelvic structure, an extremity structure, an intracranial structure, a cerebrospinal fluid space, a brain structure, a dental structure, a nervous structure, a spinal structure, a cardiovascular structure, a heart structure, a heart valve, a heart chamber, a pericardial structure, a vascular structure, a calcified vascular structure, a lung structure, an emphysematous structure, a pleural structure, a mediastinal structure, an esophageal structure, a thoracic muscle structure, a thoracic wall structure, a thoracic fat structure, a mammary or breast structure, an endocrine structure, a liver structure, a gallbladder structure, a biliary structure, a pancreas structure, a spleen structure, an adrenal structure, a kidney structure, a stomach or bowel structure, a body wall structure, an abdominal muscle structure, an abdominal fat structure, a subcutaneous fat structure, a visceral fat structure, a retroperitoneal structure, a peritoneal structure, a musculoskeletal or bone structure, a reproductive structure, a prostate structure, a uterine structure, an ovarian structure, a lymph node structure, a mass structure, a nodule structure, a cystic structure, a soft tissue structure, a fluid structure, a fat structure, a calcified structure, an aerated structure, a metallic structure, a medical device, a foreign body, a surgical structure, or an artificial structure.

Act 406 of flow diagram 400 includes determining one or more key images of the one or more images of the set of input images by utilizing the one or more images as input to a key image localization module, the key image localization module being configured to receive image input and provide key image indicator output or key image output. The key image localization module may comprise one or more AI modules. In some instances, act 406 is performed in response to determining that the key structure presence indicator indicates that the one or more key structures are represented within the one or more images of the set of input images. In some instances, the one or more key images provide a largest representation of the one or more key structures within the set of input images.

Act 408 of flow diagram 400 includes determining key structure segmentation by utilizing the one or more key images as input to a key structure segmentation module, the key structure segmentation module being configured to receive image input and provide region of interest output. The key structure segmentation module may comprise one or more AI modules. In some instances, the key structure segmentation comprises segmentation for two or more bodily structures.

Act 410 of flow diagram 400 includes determining one or more patient condition metrics using the key structure segmentation.

Act 412 of flow diagram 400 includes (i) generating a report associated with the patient based upon the one or more patient condition metrics, or (ii) generating an entry at one or more practitioner worklists based upon the one or more patient condition metrics. In some instances, the entry comprises the report. In some instances, the report or the entry indicate whether the one or more patient condition metrics satisfy one or more thresholds or conditions. In some implementations, act 412 is performed in response to determining that the one or more patient condition metrics satisfy one or more thresholds or conditions. In some instances, the report or the entry comprise: identifying information for the patient, a potential patient condition based upon the one or more patient condition metrics, identifying information for the one or more key images, and/or one or more recommended practitioner actions based upon the potential patient condition. The report or the one or more practitioner worklists may be sent to a device associated with a healthcare practitioner.

In some implementations, the report or the entry are further based upon one or more additional patient condition metrics, which may be determined by: (i) determining whether one or more additional key structures are represented within the one or more images of the set of input images by utilizing the one or more images as input to an additional key structure detection module, where the one or more additional key structures are different from the one or more key structures; (ii) determine one or more additional key images of the one or more images of the set of input images by utilizing the one or more images as input to an additional key image localization module; (iii) determine additional key structure segmentation by utilizing the one or more key images as input to an additional key structure segmentation module; and (iv) determine one or more additional patient condition metrics using the additional key structure segmentation.

Act 414 of flow diagram 400 includes determining a potential patient condition based upon whether the one or more patient condition metrics satisfy one or more thresholds or conditions. In some instances, the potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition. In some implementations, the potential patient condition is further based upon output of a natural language processing module, which may be obtained by utilizing one or more medical imaging reports as input to the natural language processing module, where the one or more medical imaging reports are associated with the one or more images of the set of input images.

In some instances, act 414 further includes determining a recommended digital therapeutic based upon the potential patient condition. The digital therapeutic may be added to the report or the entry of act 412.

Act 416 of flow diagram 400 includes determining whether the potential patient condition comprises an unmanaged condition based upon (i) user input provided in response to the report or the entry at the one or more practitioner worklists or (ii) output of a natural language processing module provided by processing one or more electronic medical records associated with the patient. Act 416 may further comprise initiating contact with the patient in response to determining that the potential patient condition comprises an unmanaged condition.

A system performing any acts of flow diagram 400 (or flow diagrams 500 or 600) can be configured to send a message, notification, or letter based on the one or more patient condition metrics to the patient or one or more practitioners. For instance, the message or notification can include various findings and can indicate any unmanaged conditions that have been detected (or can omit information related to unmanaged conditions if unavailable).

Act 502 of flow diagram 500 of FIG. 5 includes determining a first potential patient condition based upon one or more first patient condition metrics, the one or more first patient condition metrics being determined using (i) first image processing output of one or more image processing modules, the first image processing output being generated using a first set of input images comprising one or more first images depicting one or more first bodily structures of a first patient and (ii) first natural language processing output of one or more natural language processing modules, the first natural language processing output being generated using one or more first medical imaging reports associated with the first patient.

In some implementations, the first potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition. The first potential patient condition may be determined to be a first unmanaged condition. In some implementations, the first set of input images comprises one or more radiography images, computed tomography images, magnetic resonance imaging images, positron emission tomography images, or ultrasound images.

In some examples, the one or more image processing modules comprise one or more of: a key structure detection module configured to receive image input and provide key structure presence indicator output based upon the image input, a key image localization module configured to receive image input and provide key image indicator output or key image output, or a key structure segmentation module configured to receive image input and provide region of interest output. In some instances, the first potential patient condition is based upon one or more first patient condition metrics determined using region of interest output of the key structure segmentation module.

Act 504 of flow diagram 500 includes generating a first entry for the first patient at a practitioner worklist based upon the first potential patient condition. In some instances, the first entry comprises: identifying information for the first patient, the first potential patient condition, identifying information for one or more first key images of the first set of input images, and/or one or more recommended practitioner actions based upon the first potential patient condition.

Act 506 of flow diagram 500 includes determining a second potential patient condition based upon one or more second patient condition metrics, the one or more second patient condition metrics being determined using (i) second image processing output of the one or more image processing modules, the second image processing output being generated using a second set of input images comprising one or more second images depicting one or more second bodily structures of a second patient and (ii) second natural language processing output of the one or more natural language processing modules, the second natural language processing output being generated using one or more second medical imaging reports associated with the second patient.

In some implementations, the second potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition. The second potential patient condition may be determined to be a second unmanaged condition. In some implementations, the second set of input images comprises one or more radiography images, computed tomography images, magnetic resonance imaging images, positron emission tomography images, or ultrasound images.

In some examples, the one or more image processing modules comprise one or more of: a key structure detection module configured to receive image input and provide key structure presence indicator output based upon the image input, a key image localization module configured to receive image input and provide key image indicator output or key image output, or a key structure segmentation module configured to receive image input and provide region of interest output. In some instances, the second potential patient condition is based upon one or more second patient condition metrics determined using region of interest output of the key structure segmentation module.

Act 508 of flow diagram 500 includes generating a second entry for the second patient at the practitioner worklist based upon the second potential patient condition. In some instances, the second entry comprises: identifying information for the second patient, the second potential patient condition, identifying information for one or more second key images of the second set of input images, and/or one or more recommended practitioner actions based upon the second potential patient condition.

Act 602 of flow diagram 600 of FIG. 6 includes determining a potential patient condition based upon one or more patient condition metrics, the one or more patient condition metrics being determined using image processing output of one or more image processing modules, the image processing output being generated using a set of input images comprising one or more images depicting one or more bodily structures of a patient. In some instances, the potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition. In some implementations, the set of input images comprises one or more radiography images, computed tomography images, magnetic resonance imaging images, positron emission tomography images, or ultrasound images.

In some instances, the one or more image processing modules comprise one or more of: a key structure detection module configured to receive image input and provide key structure presence indicator output based upon the image input, a key image localization module configured to receive image input and provide key image indicator output or key image output, or a key structure segmentation module configured to receive image input and provide region of interest output. In some examples, the potential patient condition is based upon one or more patient condition metrics determined using region of interest output of the key structure segmentation module. In some implementations, determining the potential patient condition is further based upon natural language processing output of one or more natural language processing modules, the natural language processing output being generated using one or more medical imaging reports or electronic medical records associated with the patient.

In some implementations, the potential patient condition is determined to be an unmanaged condition based upon (i) user input provided in response to a report or worklist entry indicating the potential patient condition or (ii) the natural language processing output.

Act 604 of flow diagram 600 includes determining or configuring a recommended digital therapeutic based upon the potential patient condition for the patient.

Act 606 of flow diagram 600 includes adding the recommended digital therapeutic to a report or an entry of a practitioner worklist in association with the patient. In some implementations, act 606 includes prescribing of the recommended digital therapeutic by a healthcare provider/practitioner. In some instances, act 606 includes enrolling the patient into the recommended digital therapeutic and/or causing installation of an application (e.g., a mobile application) associated with the recommended digital therapeutic on a mobile electronic device associated with the patient.

Act 608 of flow diagram 600 includes associating the patient with a patient care network based upon the potential patient condition.

Embodiments disclosed herein can include those in the following numbered clauses:

Clause 1. A system, comprising: one or more processors; and one or more hardware storage devices that store instructions that are executable by the one or more processors to configure the system to: obtain a set of input images, the set of input images comprising one or more images, each of the one or more images depicting one or more bodily structures of a patient; determine whether one or more key structures are represented within the one or more images of the set of input images by utilizing the one or more images as input to a key structure detection module, the key structure detection module being configured to receive image input and provide key structure presence indicator output based upon the image input; determine one or more key images of the one or more images of the set of input images by utilizing the one or more images as input to a key image localization module, the key image localization module being configured to receive image input and provide key image indicator output or key image output; determine key structure segmentation by utilizing the one or more key images as input to a key structure segmentation module, the key structure segmentation module being configured to receive image input and provide region of interest output; determine one or more patient condition metrics using the key structure segmentation; and (i) generate a report associated with the patient based upon the one or more patient condition metrics, or (ii) generate an entry at one or more practitioner worklists based upon the one or more patient condition metrics.

Clause 2. The system of clause 1, wherein the set of input images comprises one or more radiography images, computed tomography images, magnetic resonance imaging images, positron emission tomography images, or ultrasound images.

Clause 3. The system of clause 1, wherein the one or more key structures comprise one or more of: an organ, a body compartment, a cranial structure, a neck structure, a thoracic structure, an abdominal structure, a pelvic structure, an extremity structure, an intracranial structure, a cerebrospinal fluid space, a brain structure, a dental structure, a nervous structure, a spinal structure, a cardiovascular structure, a heart structure, a heart valve, a heart chamber, a pericardial structure, a vascular structure, a calcified vascular structure, a lung structure, an emphysematous structure, a pleural structure, a mediastinal structure, an esophageal structure, a thoracic muscle structure, a thoracic wall structure, a thoracic fat structure, a mammary or breast structure, an endocrine structure, a liver structure, a gallbladder structure, a biliary structure, a pancreas structure, a spleen structure, an adrenal structure, a kidney structure, a stomach or bowel structure, a body wall structure, an abdominal muscle structure, an abdominal fat structure, a subcutaneous fat structure, a visceral fat structure, a retroperitoneal structure, a peritoneal structure, a musculoskeletal or bone structure, a reproductive structure, a prostate structure, a uterine structure, an ovarian structure, a lymph node structure, a mass structure, a nodule structure, a cystic structure, a soft tissue structure, a fluid structure, a fat structure, a calcified structure, an aerated structure, a metallic structure, a medical device, a foreign body, a surgical structure, or an artificial structure.

Clause 4. The system of clause 1, wherein the key structure presence indicator output comprises binary output indicating whether the one or more key structures are present in any of the one or more images of the set of input images.

Clause 5. The system of clause 1, wherein the instructions are executable by the one or more processors to configure the system to determine the one or more key images of the one or more images of the set of input images in response to determining that the key structure presence indicator indicates that the one or more key structures are represented within the one or more images of the set of input images.

Clause 6. The system of clause 1, wherein the one or more key images provide a largest representation of the one or more key structures within the set of input images.

Clause 7. The system of clause 1, wherein the key structure segmentation comprises segmentation for two or more bodily structures.

Clause 8. The system of clause 1, wherein the report or the entry indicate whether the one or more patient condition metrics satisfy one or more thresholds or conditions.

Clause 9. The system of clause 1, wherein the instructions are executable by the one or more processors to configure the system to generate the report or generate the entry at the one or more practitioner worklists in response to determining that the one or more patient condition metrics satisfy one or more thresholds or conditions.

Clause 10. The system of clause 1, wherein the report or the entry comprise: identifying information for the patient; a potential patient condition based upon the one or more patient condition metrics; identifying information for the one or more key images; and/or one or more recommended practitioner actions based upon the potential patient condition.

Clause 11. The system of clause 10, wherein the potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition.

Clause 12. The system of clause 1, wherein the instructions are executable by the one or more processors to further configure the system to send the report or the one or more practitioner worklists to a device associated with a healthcare practitioner.

Clause 13. The system of clause 1, wherein the entry comprises the report.

Clause 14. The system of clause 1, wherein the instructions are executable by the one or more processors to further configure the system to determine a potential patient condition based upon whether the one or more patient condition metrics satisfy one or more thresholds or conditions.

Clause 15. The system of clause 14, wherein the instructions are executable by the one or more processors to further configure the system to utilize one or more medical imaging reports as input to a natural language processing module, the one or more medical imaging reports being associated with the one or more images of the set of input images.

Clause 16. The system of clause 15, wherein the potential patient condition is further based upon output of the natural language processing module.

Clause 17. The system of clause 14, wherein the instructions are executable by the one or more processors to further configure the system to: determine whether the potential patient condition comprises an unmanaged condition based upon (i) user input provided in response to the report or the entry at the one or more practitioner worklists or (ii) output of a natural language processing module provided by processing one or more electronic medical records associated with the patient.

Clause 18. The system of clause 1, wherein the instructions are executable by the one or more processors to further configure the system to: determine a potential patient condition based upon whether the one or more patient condition metrics satisfy one or more thresholds or conditions; and determine a recommended digital therapeutic based upon the potential patient condition.

Clause 19. The system of clause 18, wherein the report or the entry comprise the recommended digital therapeutic.

Clause 20. The system of clause 1, wherein the key structure detection module, the key image localization module, and the key structure segmentation module comprise artificial intelligence modules.

Clause 21. The system of clause 1, wherein the instructions are executable by the one or more processors to further configure the system to: determine whether one or more additional key structures are represented within the one or more images of the set of input images by utilizing the one or more images as input to an additional key structure detection module, wherein the one or more additional key structures are different from the one or more key structures; determine one or more additional key images of the one or more images of the set of input images by utilizing the one or more images as input to an additional key image localization module; determine additional key structure segmentation by utilizing the one or more key images as input to an additional key structure segmentation module; and determine one or more additional patient condition metrics using the additional key structure segmentation.

Clause 22. The system of clause 21, wherein the report or the entry are further based on the one or more additional patient condition metrics.

Clause 23. The system of clause 21, wherein the instructions are executable by the one or more processors to further configure the system to: determine a potential patient condition based upon the one or more patient condition metrics, the one or more practitioner worklists being associated with the potential patient condition; determine an additional potential patient condition based upon the one or more additional patient condition metrics; and generate an additional entry at one or more additional practitioner worklists based upon the one or more additional patient condition metrics, the one or more additional practitioner worklists being associated with the additional potential patient condition.

Clause 24. The system of clause 1, wherein the instructions are executable by the one or more processors to further configure the system to send a message or notification based on the one or more patient condition metrics to the patient or one or more practitioners.

Clause 25. A system, comprising: one or more processors; and one or more hardware storage devices that store instructions that are executable by the one or more processors to configure the system to: determine a first potential patient condition based upon one or more first patient condition metrics, the one or more first patient condition metrics being determined using (i) first image processing output of one or more image processing modules, the first image processing output being generated using a first set of input images comprising one or more first images depicting one or more first bodily structures of a first patient and (ii) first natural language processing output of one or more natural language processing modules, the first natural language processing output being generated using one or more first medical imaging reports associated with the first patient; generate a first entry for the first patient at a practitioner worklist based upon the first potential patient condition; determine a second potential patient condition based upon one or more second patient condition metrics, the one or more second patient condition metrics being determined using (i) second image processing output of the one or more image processing modules, the second image processing output being generated using a second set of input images comprising one or more second images depicting one or more second bodily structures of a second patient and (ii) second natural language processing output of the one or more natural language processing modules, the second natural language processing output being generated using one or more second medical imaging reports associated with the second patient; and generate a second entry for the second patient at the practitioner worklist based upon the second potential patient condition.

Clause 26. The system of clause 25, wherein the first set of input images or the second set of input images comprises one or more radiography images, computed tomography images, magnetic resonance imaging images, positron emission tomography images, or ultrasound images.

Clause 27. The system of clause 25, wherein the one or more image processing modules comprise one or more of: a key structure detection module configured to receive image input and provide key structure presence indicator output based upon the image input, a key image localization module configured to receive image input and provide key image indicator output or key image output, or a key structure segmentation module configured to receive image input and provide region of interest output.

Clause 28. The system of clause 27, wherein the first potential patient condition or the second potential patient condition is based upon one or more first patient condition metrics or one or more second patient condition metrics, respectively, determined using region of interest output of the key structure segmentation module.

Clause 29. The system of clause 25, wherein the first entry or the second entry comprises: identifying information for the first patient or the second patient, respectively; the first potential patient condition or the second potential patient condition, respectively; identifying information for one or more first key images of the first set of input images or for one or more second key images of the second set of input images, respectively; and/or one or more recommended practitioner actions based upon the first potential patient condition or the second potential patient condition, respectively.

Clause 30. The system of clause 25, wherein the first potential patient condition and the second potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition.

Clause 31. The system of clause 25, wherein the first potential patient condition is determined to be a first unmanaged condition, or wherein the second potential patient condition is determined to be a second unmanaged condition.

Clause 32. A system, comprising: one or more processors; and one or more hardware storage devices that store instructions that are executable by the one or more processors to configure the system to: determine a potential patient condition based upon one or more patient condition metrics, the one or more patient condition metrics being determined using image processing output of one or more image processing modules, the image processing output being generated using a set of input images comprising one or more images depicting one or more bodily structures of a patient; and determine a recommended digital therapeutic based upon the potential patient condition for the patient.

Clause 33. The system of clause 32, wherein the set of input images comprises one or more radiography images, computed tomography images, magnetic resonance imaging images, positron emission tomography images, or ultrasound images.

Clause 34. The system of clause 32, wherein the one or more image processing modules comprise one or more of: a key structure detection module configured to receive image input and provide key structure presence indicator output based upon the image input, a key image localization module configured to receive image input and provide key image indicator output or key image output, or a key structure segmentation module configured to receive image input and provide region of interest output.

Clause 35. The system of clause 34, wherein the potential patient condition is based upon one or more patient condition metrics determined using region of interest output of the key structure segmentation module.

Clause 36. The system of clause 32, wherein the potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition.

Clause 37. The system of clause 32, wherein determining the potential patient condition is further based upon natural language processing output of one or more natural language processing modules, the natural language processing output being generated using one or more medical imaging reports or electronic medical records associated with the patient.

Clause 38. The system of clause 37, wherein the potential patient condition is determined to be an unmanaged condition based upon (i) user input provided in response to a report or worklist entry indicating the potential patient condition or (ii) the natural language processing output.

Clause 39. The system of clause 32, wherein the instructions are executable by the one or more processors to further configure the system to add the recommended digital therapeutic to a report or an entry of a practitioner worklist in association with the patient.

Clause 40. The system of clause 32, wherein the instructions are executable by the one or more processors to further configure the system to associate the patient with a patient care network based upon the potential patient condition.

Additional Details Related to Implementing the Disclosed Embodiments

The principles disclosed herein may be implemented in various formats. For example, the various techniques discussed herein may be performed as a method that includes various acts for achieving particular results or benefits. In some instances, the techniques discussed herein are represented in computer-executable instructions that may be stored on one or more hardware storage devices. The computer-executable instructions may be executable by one or more processors to carry out (or to configure a system to carry out) the disclosed techniques. In some embodiments, a system may be configured to send the computer-executable instructions to a remote device to configure the remote device for carrying out the disclosed techniques.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system.

Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media (e.g., hardware storage devices) and transmission computer-readable media.

Physical computer-readable storage media includes hardware storage devices such as RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g., as separate threads).

CONCLUSION

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

Unless defined otherwise, all technical and scientific terms used herein have the same meaning as commonly understood by one of ordinary skill in the art to which the present disclosure pertains.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A system, comprising:
one or more processors; and
one or more hardware storage devices that store instructions that are executable by the one or more processors to configure the system to:
obtain a set of input images, the set of input images comprising one or more images, each of the one or more images depicting one or more bodily structures of a patient;
determine whether one or more key structures are represented within the one or more images of the set of input images by utilizing the one or more images as input to a key structure detection module, the key structure detection module being configured to receive image input and provide key structure presence indicator output based upon the image input;
determine one or more key images of the one or more images of the set of input images by utilizing the one or more images as input to a key image localization module, the key image localization module being configured to receive image input and provide key image indicator output or key image output;
determine key structure segmentation by utilizing the one or more key images as input to a key structure segmentation module, the key structure segmentation module being configured to receive image input and provide region of interest output;
determine one or more patient condition metrics using the key structure segmentation; and
(i) generate a report associated with the patient based upon the one or more patient condition metrics, or
(ii) generate an entry at one or more practitioner worklists based upon the one or more patient condition metrics.

2. The system of claim 1, wherein the one or more key structures comprise one or more of: an organ, a body compartment, a cranial structure, a neck structure, a thoracic structure, an abdominal structure, a pelvic structure, an extremity structure, an intracranial structure, a cerebrospinal fluid space, a brain structure, a dental structure, a nervous structure, a spinal structure, a cardiovascular structure, a heart structure, a heart valve, a heart chamber, a pericardial structure, a vascular structure, a calcified vascular structure, a lung structure, an emphysematous structure, a pleural structure, a mediastinal structure, an esophageal structure, a thoracic muscle structure, a thoracic wall structure, a thoracic fat structure, a mammary or breast structure, an endocrine structure, a liver structure, a gallbladder structure, a biliary structure, a pancreas structure, a spleen structure, an adrenal structure, a kidney structure, a stomach or bowel structure, a body wall structure, an abdominal muscle structure, an abdominal fat structure, a subcutaneous fat structure, a visceral fat structure, a retroperitoneal structure, a peritoneal structure, a musculoskeletal or bone structure, a reproductive structure, a prostate structure, a uterine structure, an ovarian structure, a lymph node structure, a mass structure, a nodule structure, a cystic structure, a soft tissue structure, a fluid structure, a fat structure, a calcified structure, an aerated structure, a metallic structure, a medical device, a foreign body, a surgical structure, or an artificial structure.

3. The system of claim 1, wherein the one or more key images provide a largest representation of the one or more key structures within the set of input images, or wherein the key structure segmentation comprises segmentation for two or more bodily structures.

4. The system of claim 1, wherein the report or the entry indicate whether the one or more patient condition metrics satisfy one or more thresholds or conditions, or wherein the instructions are executable by the one or more processors to configure the system to generate the report or generate the entry at the one or more practitioner worklists in response to determining that the one or more patient condition metrics satisfy one or more thresholds or conditions.

5. The system of claim 1, wherein the report or the entry comprise:
identifying information for the patient;
a potential patient condition based upon the one or more patient condition metrics;
identifying information for the one or more key images; and/or
one or more recommended practitioner actions based upon the potential patient condition.

6. The system of claim 5, wherein the potential patient condition comprises one or more of: a neurologic condition, a dental condition, a cardiovascular condition, an endocrine condition, a pulmonary condition, a mammary condition, a musculoskeletal condition, a bone density condition, a gastrointestinal condition, a genitourinary condition, a liver condition, a biliary condition, a gallbladder condition, a pancreatic condition, a spleen condition, an adrenal condition, a kidney condition, a lymph node condition, a metabolic condition, a cancer condition, or a reproductive condition.

7. The system of claim 1, wherein the instructions are executable by the one or more processors to further configure the system to determine a potential patient condition based upon whether the one or more patient condition metrics satisfy one or more thresholds or conditions.

8. The system of claim 7, wherein the instructions are executable by the one or more processors to further configure the system to utilize one or more medical imaging reports as input to a natural language processing module, the one or more medical imaging reports being associated with the one or more images of the set of input images, wherein the potential patient condition is further based upon output of the natural language processing module.

9. The system of claim 7, wherein the instructions are executable by the one or more processors to further configure the system to:
determine whether the potential patient condition comprises an undiagnosed or untreated condition based upon (i) user input provided in response to the report or the entry at the one or more practitioner worklists or (ii) output of a natural language processing module provided by processing one or more electronic medical records associated with the patient.

10. The system of claim 1, wherein the instructions are executable by the one or more processors to further configure the system to send a message, notification, or letter based on the one or more patient condition metrics to the patient or one or more practitioners.

11. A system, comprising:
one or more processors; and
one or more hardware storage devices that store instructions that are executable by the one or more processors to configure the system to:
determine a potential patient condition based upon one or more patient condition metrics, the one or more patient condition metrics being determined using image processing output of one or more image processing modules, the image processing output being generated using a set of input images comprising one or more images depicting one or more bodily structures of a patient, wherein determining the potential patient condition is further based upon natural language processing output of one or more natural language processing modules, the natural language processing output being generated using one or more medical imaging reports or electronic medical records associated with the patient, wherein the potential patient condition is determined to be an undiagnosed or untreated condition based upon (i) user input provided in response to a report or worklist entry indicating the potential patient condition or (ii) the natural language processing output; and
determine a recommended digital therapeutic based upon the potential patient condition for the patient.

12. The system of claim 11, wherein the one or more image processing modules comprise one or more of: a key structure detection module configured to receive image input and provide key structure presence indicator output based upon the image input, a key image localization module configured to receive image input and provide key image indicator output or key image output, or a key structure segmentation module configured to receive image input and provide region of interest output.

13. The system of claim 12, wherein the one or more image processing modules comprises at least the key structure segmentation module, and wherein the potential patient condition is based upon one or more patient condition metrics determined using region of interest output of the key structure segmentation module.

14. The system of claim 11, wherein the instructions are executable by the one or more processors to further configure the system to: add the recommended digital therapeutic to a report or an entry of a practitioner worklist in association with the patient, or associate the patient with a patient care network based upon the potential patient condition.

* * * * *